United States Patent [19]
Henwood

[11] Patent Number: 6,132,086
[45] Date of Patent: *Oct. 17, 2000

[54] SINGLE USE INDICATOR FOR MEDICAL THERMOMETERS

[76] Inventor: Peter S. W. Henwood, 72 New Bond Street, London, United Kingdom, W1Y 9DD

[*] Notice: This patent is subject to a terminal disclaimer.

[21] Appl. No.: 09/119,246

[22] Filed: Jul. 20, 1998

Related U.S. Application Data

[63] Continuation-in-part of application No. 08/859,653, May 20, 1997, Pat. No. 5,813,992.

[51] Int. Cl.⁷ ...................................................... G01K 1/08
[52] U.S. Cl. ................................ 374/158; 73/73; 374/209
[58] Field of Search .................................. 374/158, 161, 374/143, 209; 116/208; 73/73

[56] References Cited

U.S. PATENT DOCUMENTS

| | | | |
|---|---|---|---|
| 3,731,685 | 5/1973 | Eidus | 116/206 |
| 3,881,873 | 5/1975 | Klowden | 116/206 |
| 4,072,054 | 2/1978 | Blouin et al. | 374/158 |
| 4,184,445 | 1/1980 | Burrows | 116/206 |
| 4,201,080 | 5/1980 | Slepak et al. | 116/206 |
| 5,008,136 | 4/1991 | Chamberlain | 374/161 |
| 5,322,031 | 6/1994 | Lerner et al. | 116/208 |
| 5,813,992 | 9/1998 | Henwood | 600/528 |

*Primary Examiner*—G. Bradley Bennett
*Assistant Examiner*—Gail Verbitsky
*Attorney, Agent, or Firm*—Michael I. Kroll

[57] ABSTRACT

The present invention relates to a protective cover for a medical thermometer with a temperature probe region which is placed in direct contact with a patient during use. The cover is disposable and adapted to be removably secured to the temperature probe region such that the cover completely covers the temperature probe region, thereby physically isolating the temperature probe region from contaminants, and further includes means for effecting a visual change in the appearance of the cover when the thermometer is used. The cover is preferably formed of a thin, elastomeric, liquid-impervious material and its appearance changes upon exposure to one or more of moisture, pressure, galvanic skin response and skin temperature.

7 Claims, 5 Drawing Sheets

SINGLE USE INDICATOR FOR MEDICAL THERMOMETERS

CROSS-REFERENCE TO RELATED APPLICATION

This application is a continuation-in-part of my application Ser. No. 08/859,653, filed May 20, 1997, now U.S. Pat. No. 5,813,992 entitled "Single Use Indicator for Stethoscopes," which is incorporated herein by this reference.

BACKGROUND OF THE INVENTION

1. Field of the Invention

The instant invention relates generally to single use, disposable covers for protecting medical thermometers from contamination by physical contact with the patient. More specifically, it relates to thermometer covers having a visually perceptible indication of use, so that the thermometer user can readily determine if the thermometer has been used, in order to ensure that contaminants are not transferred between patients. The invention also relates to single use disposable medical thermometers having a visually perceptible indication of use.

2. Description of the Prior Art

Protective covers for stethoscopes are known in the art. For example, U.S. Pat. No. 5,365,023 (Lawton, G. P., Nov. 15, 1994) discloses an elastic, disposable cover for the head of stethoscope, formed of latex or a similar elastomeric material, preferably pre-shaped in a shallow parabola to facilitate installation and removal.

U.S. Pat. No. 5,428,193 (Mandiberg, R., Jun. 27, 1995) discloses a flexible, resilient and removable cover for temporarily covering the diaphragm portion of a stethoscope.

U.S. Pat. No. 5,528,004 (Wurzburger, I., Jun. 18, 1996) discloses a disk-shaped structure having an adhesive backing for attachment to the diaphragm of the stethoscope.

BRIEF SUMMARY OF THE INVENTION

The present invention is concerned with the aseptic use of medical thermometers. Specifically, the invention relates to thermometer covers having a visually perceptible indication of use and also to disposable, single use thermometers having a visually perceptible indication of use.

A primary object of the present invention is to provide a protective thermometer cover which reduces the chances of spreading contamination between patients by providing a visually perceptible indication that the cover has been used on a patient.

Another object of the present invention is to provide a protective thermometer cover which can be removably attached to the temperature probe portion of a thermometer and which undergoes a visually perceptible change upon contact with the patient.

An additional object of the present invention is to provide a protective thermometer cover which undergoes a visually perceptible change in color or opacity as a result of exposure to one of more of moisture, pressure, skin temperature and galvanic skin response.

A further object of the present invention is to provide a disposable (single-use) medical thermometer which undergoes a visually perceptible change upon use, so that the thermometer is not reused on a subsequent patient.

Another object of the present invention is to provide a protective thermometer cover which is simple to make and easy to use.

Another object is to provide a protective thermometer cover that is economical in cost to manufacture.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DETAILED DESCRIPTION OF THE PREFERRED EMBODIMENTS

Figure 1:
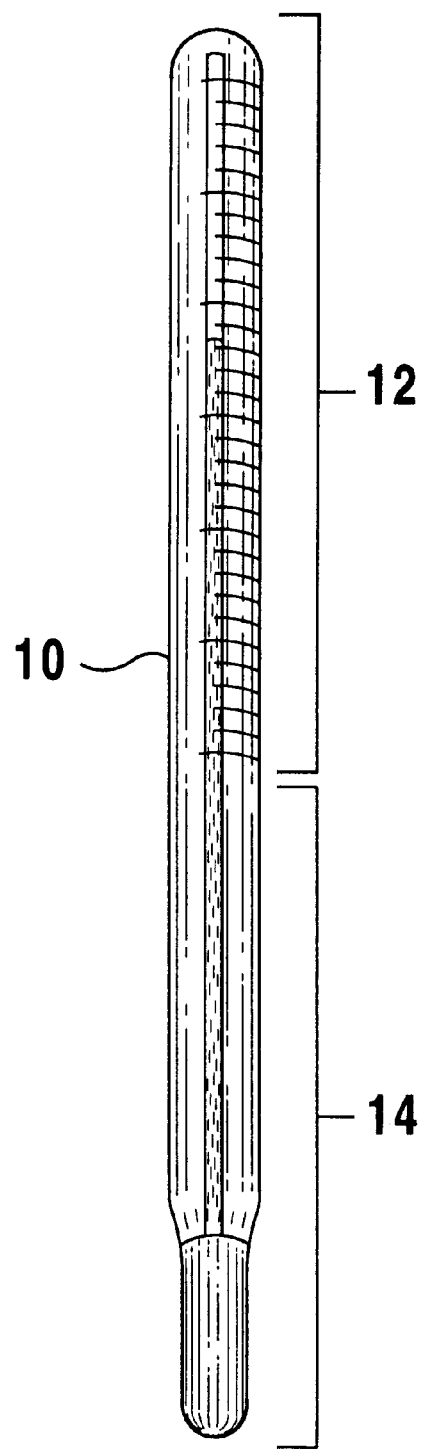
FIG. 1 is an overview of a typical medical thermometer.

Turning now descriptively to the drawings, in which similar reference characters denote similar elements throughout the several views, the Figures illustrate a single use thermometer cover of the present invention. With regard to the reference numerals used, the following numbering is used throughout the various drawing figures.

10 medical thermometer
12 temperature display region of 10
14 temperature probe region of 10
16 disposable, protective cover for 10
18 mouth of patient using 10
20 tongue of 18
22 support layer of 16
24 use indicating layer of 16, before use
26 use indicating layer of 16, after use FIGS. 1 through 7 illustrate a thermometer cover 10 having a single use indicator adapted to be removably secured to the temperature probe region 14 of a medical thermometer 10. Most medical thermometers are generally cylindrical in shape and have a temperature display region 12 at one end and a temperature probe region 14 at the other end which is placed in contact with a patient during use. The most common types of medical thermometers are designed for specific portions of the body, for example, oral, rectal otic and axillary thermometers are all known in the art. The present invention is effective and appropriate for all of these applications, and any other thermometers and other medical devices which are placed in contact with a patient.

Figure 2:
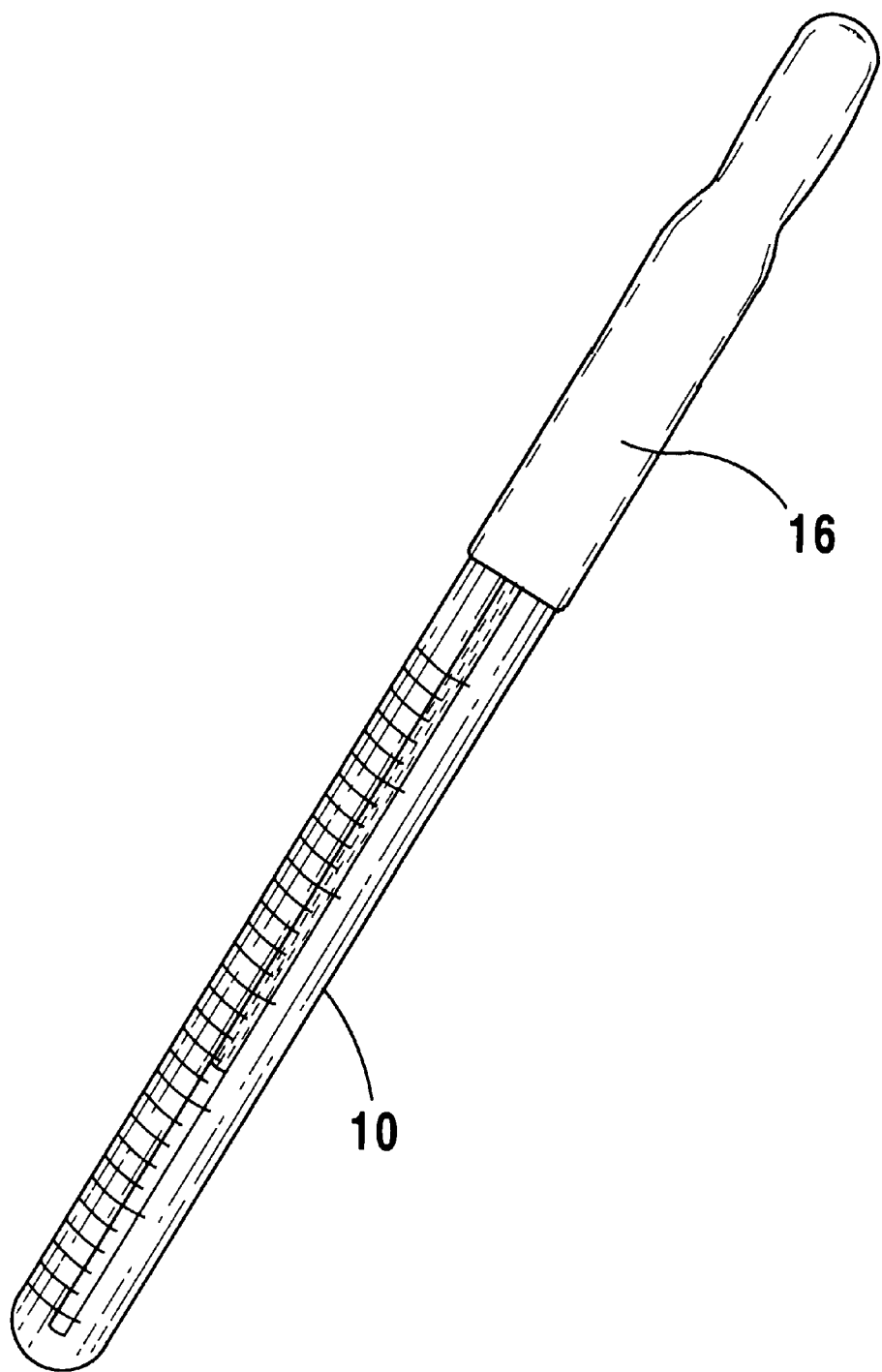
FIG. 2 is an overview of a typical medical thermometer utilizing the single use thermometer cover of the present invention.
Figure 3:
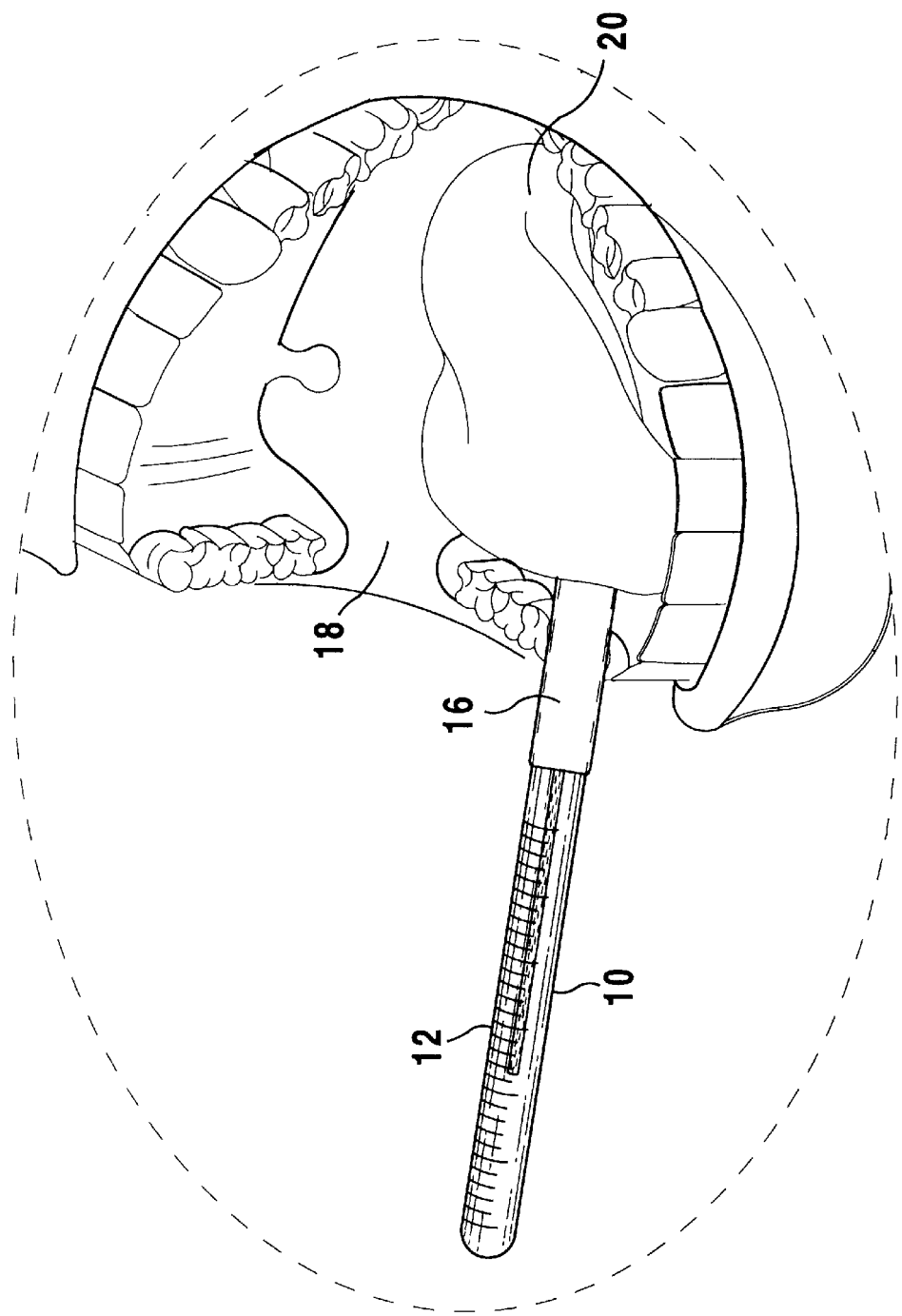
FIG. 3 is an overview of a typical oral medical thermometer and single use thermometer cover of the present invention in use.

FIGS. 1 and 2 illustrate a thermometer 10 without (FIG. 1) and with (FIG. 2) the cover 16 of the present invention in place. The thermometer cover of the present invention is adapted to be removably secured to the thermometer 10 such that the temperature probe region 14 of the thermometer is completely covered, thereby physically isolating the temperature probe region 14 from contamination by the patient. FIG. 3 illustrates a thermometer 10 with a protective cover 16 in place, being used by placement under the tongue 20 in the mouth 18 of a patient. As can be seen in the figure, the cover 16 completely isolates the thermometer from the mouth 18 of the patient, thereby preventing contamination of the thermometer.

In order to 1) protect the temperature probe region 14 from contamination and 2) allow normal functioning of the thermometer, the cover is preferably made from a thin, elastomeric, liquid-impervious material such as, for example, latex. In its preferred embodiment, the cover is generally cylindrical in shape, so that it snugly engages the temperature probe region 14 of the thermometer 10, thereby providing complete coverage of the temperature probe region 14, the portion which comes in contact with the patient. In one embodiment of the invention the thermometer cover has a spiral rolled or raised edge, similar to that of a condom, in order to facilitate placement and removal, and also to ensure a snug fit.

The thermometer cover of the present invention can take other forms than that described above, provided that the temperature probe region 14 of the thermometer 10 is completely covered. For example, a thermometer might not be generally cylindrical such as having a flattened end to facilitate thermal conduction. It is within the scope of the present invention to provide thermometer covers which can be readily applied to and removed from any medical thermometer. The present invention is intended to encompass all forms of protective thermometer covers, as long as they include a visually perceptible indication of use. This use indicator greatly improves the efficacy of the thermometer cover by providing a readily detectable indication that the thermometer cover has been used on a patient, is potentially contaminated, and should be replaced before the thermometer is use don another patient. This avoids a major problem with known thermometer covers, namely, that there is no way to determine if the cover has been used on a patient. It can be readily appreciated that reusing a protective thermometer cover greatly diminishes its effectiveness in preventing the spread of contaminants between patients.

Figure 4:
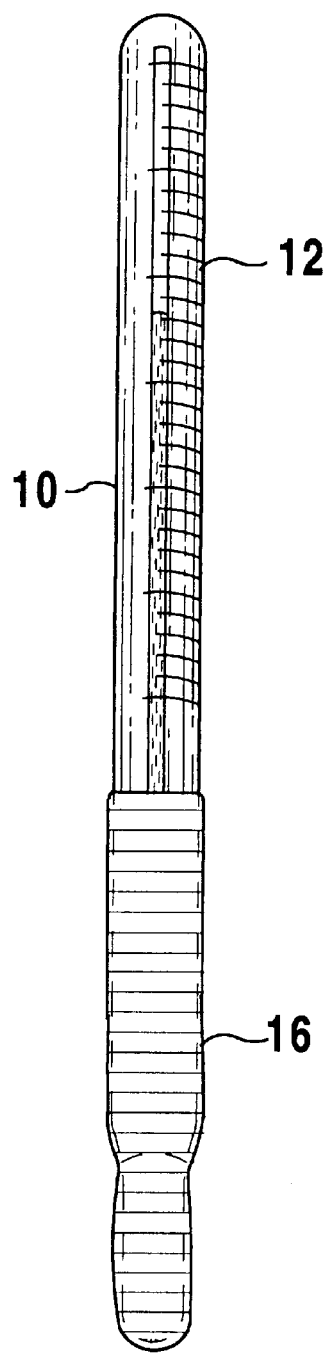
FIG. 4 is an overview of a medical thermometer and single use thermometer cover of the present invention before usage.
Figure 5:
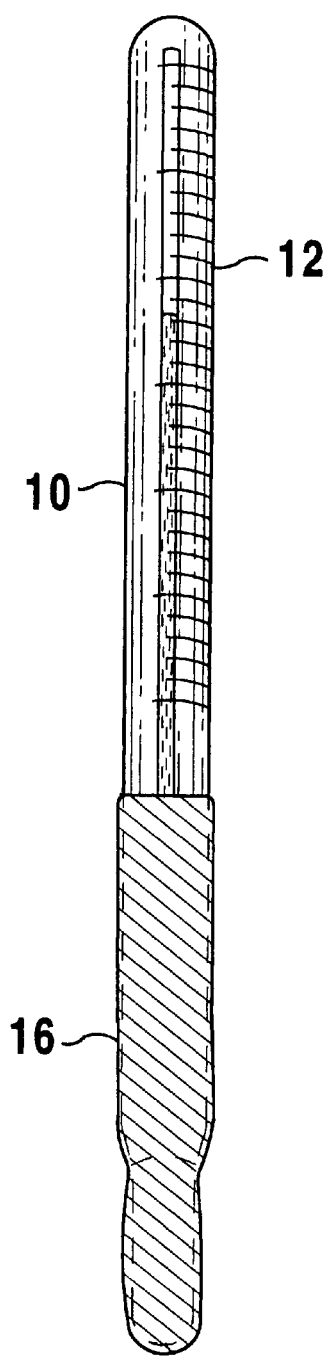
FIG. 5 is an overview of a medical thermometer and single use thermometer cover of the present invention after usage.

The visually perceptible indication of use can be triggered by one or more of various factors, all of which are within the scope of the invention. For example, the thermometer covers of the present invention can be designed to change color or opacity when exposed to one or more of the following: moisture, pressure, skin temperature or galvanic skin response. FIGS. 4 and 5 illustrate a thermometer cover of the present invention before (FIG. 4) and after (FIG. 5) being used on a patient, with the cover having undergone a visually perceptible change in appearance after usage.

Figure 6:
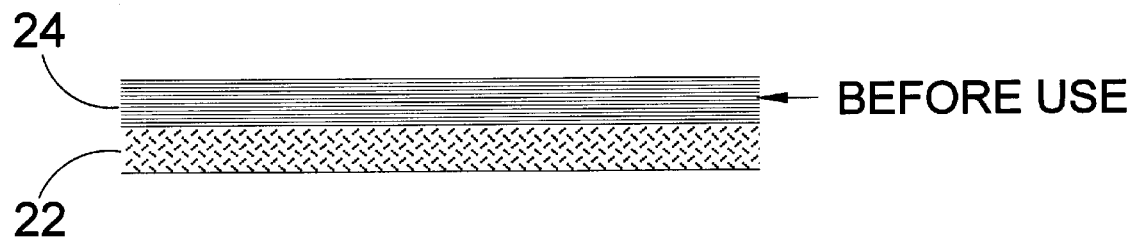
FIG. 6 is an enlarged, cross-sectional view of one embodiment of the single use medical thermometer cover of the present invention, wherein the thermometer cover material comprises a bilayer composite structure.
Figure 7:
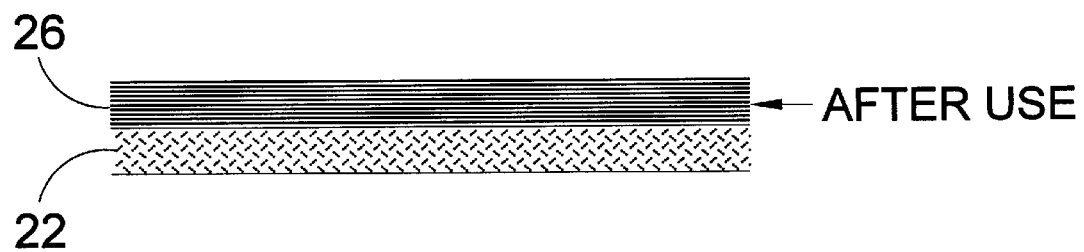
FIG. 7 is a view identical to that of FIG. 8, illustrating the visual change in appearance of one of the layers after use.

The visually perceptible use indicator can be either impregnated within the cover material, or can be disposed over the cover material as shown in FIGS. 6 and 7. If disposed over the cover material, the indicator can be either laminated securely over the cover or loosely oriented, such that the indicator is removed upon use, thus effecting the visual change.

Thermotropic materials are known in the art. See, for example, U.S. Pat. No. 4,188,437 (Rohowetz). Speaking generally, these materials include thermotropic dyes which exhibit a visible color change upon exposure to a specific threshold temperature. There are many thousands of compounds available which are thermochromic at various temperatures; selection is a simple design choice. For the instant invention, the thermotropic dye should exhibit a visible color change at a temperature of from about 90 to about 95° F. (about 32° to about 35° C.).

Materials which change color upon exposure to humidity are also known in the art. These materials include, for example, metallic salts which change color upon exposure to moisture or humidity, which exposure change the salt from its dehydrated to its hydrated form. Examples include cobalt salts, such as cobaltous chloride, but again, there are many compounds to choose from, with the particular compound or combination of compounds a simple design choice.

Pressure sensitive compositions are also well known in the art, commonly comprising a plurality of adjacent dye layers which, when pressed together, combine sufficiently to exhibit a visible color change.

With regard to galvanic skin response, it is expected that conductive inks can be suitably unemployed in the present invention. For example, the cover can have on its surface a plurality of separate conductive ink patterns which are electrically connected to each other, whereby, upon being simultaneously placed in contact with skin, the patterns are actuated by resistor bridging, resulting in a perceptible change in the ink patterns.

It will be understood that each of the elements described above, or two or more together, may also find a useful application in other types of applications differing from the type described above. While the invention has been illustrated and described as embodied in a thermometer cover with a single use indicator, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims.

What is claimed is:

1. A single use indicator for a reusable medical thermometer having a temperature probe region adapted to be placed in direct contact with a patient during use, comprising:

a) means for physically isolating said temperature probe region from contaminants comprising a disposable cover removably secured to the temperature probe region when said probe region is in direct contact with a patient during use such that said over completely covers said region; and b) means for effecting a visual change in the appearance of said cover when the thermometer is used and said cover is exposed to moisture to avoid reuse of the cover on a subsequent patient.

2. A single use indicator for a medical thermometer as defined in claim 1, wherein the thermometer is designed for oral, otic, axillary or rectal use.

3. A single use indicator for a medical thermometer having a temperature probe region adapted to be placed in direct contact with a patient during use, comprising:

a) means for physically isolating said temperature probe region from contaminants comprising a disposable cover removably secured to the temperature probe region such that said cover completely covers said region, said cover comprising two contiguous layers, a lower support layer and an upper use indicator layer; and b) means for effecting a visual change in the appearance of said cover when the thermometer is used and said cover is exposed to moisture to avoid reuse of the cover on a subsequent patient.

4. A single use indicator for a medical thermometer as defined in claim 3, wherein said upper use indicator layer includes a compound which exhibits a color change upon exposure to moisture.

5. A disposable medical thermometer with a temperature probe region which is placed in direct contact with a patient during use, wherein said temperature probe region includes cover means for effecting a visual change in the appearance of said region at the first use of the cover means exposing said region to one or more of moisture, galvanic skin response, or human skin temperature.

6. A single use indicator for a medical thermometer as defined in claim 5, wherein the thermometer is designed for oral, otic, axillary or rectal use.

7. A single use indicator for a medical thermometer as defined in claim 1, wherein said medical thermometer has a temperature display region which remains exposed and visible when said disposable cover is secured to said temperature probe region.

\* \* \* \* \*